United States Patent [19]

Carter et al.

[11] Patent Number: 5,223,430
[45] Date of Patent: Jun. 29, 1993

[54] **SUBSPECIES OF *MICROMONOSPORA CITREA* WHICH PRODUCES ANTIBIOTIC LL-E19085 ALPHA**

[75] Inventors: Guy T. Carter, Suffern; Joseph J. Goodman, Spring Valley, both of N.Y.; David P. Labeda, Peoria, Ill.

[73] Assignee: American Cyanamid Company, Wayne, N.J.

[21] Appl. No.: 783,582

[22] Filed: Oct. 28, 1991

Related U.S. Application Data

[60] Division of Ser. No. 639,496, Jan. 9, 1991, Pat. No. 5,096,907, which is a continuation-in-part of Ser. No. 373,357, Jun. 29, 1989, abandoned, which is a continuation-in-part of Ser. No. 179,357, Apr. 8, 1988, abandoned.

[51] Int. Cl.$^5$ .................... C12N 1/20; C12N 1/00; C12P 17/18; A61K 31/44
[52] U.S. Cl. .................... 435/252.1; 435/867; 435/119; 435/252.3; 514/279
[58] Field of Search .................... 435/252.1, 822, 867, 435/119, 252.3; 514/279

[56] References Cited

U.S. PATENT DOCUMENTS 5,034,224  7/1991  Kantor et al. .................... 514/279

OTHER PUBLICATIONS

Xunchu et al, ACTA Microbiol. Sin., 16 (2), 1976, pp. 110-115 (Biosis Abstract).

*Primary Examiner*—Douglas W. Robinson
*Assistant Examiner*—Susan M. Weber
*Attorney, Agent, or Firm*—Kenneth J. Dow

[57] ABSTRACT

This disclosure describes novel antibacterial agents designated LL-E10985α, LL-E19085β, LL-E19085γ, LL-E19085ζ and LL-E19085η, having the structure:

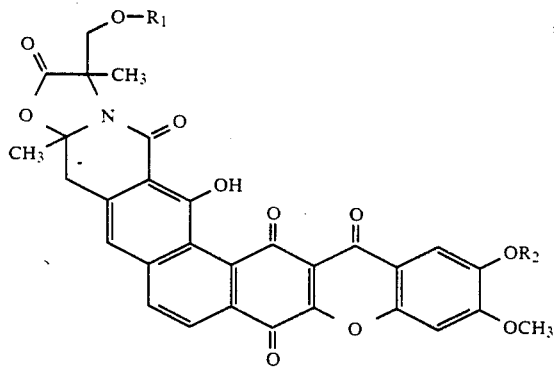

their production by aerobic fermentation of a new subspecies of *Micromonospora citrea* NRRL 18351 and mutants thereof, and the isolation and purification thereof.

1 Claim, No Drawings

SUBSPECIES OF *MICROMONOSPORA CITREA* WHICH PRODUCES ANTIBIOTIC LL-E19085 ALPHA

SUMMARY OF THE INVENTION

This application is a divisional of application Ser. No. 07/639,496, filed on Jan. 9, 1991, now U.S. Pat. No. 5,096,907, which is a continuation-in-part of application Ser. No. 07/373,357, filed Jun. 29, 1989, now abandoned, which is a continuation-in-part of application Ser. No. 07/179,357, filed Apr. 8, 1988, now abandoned.

This invention relates to new antibacterial agents designated LL-E19085γ, LL-E19085β, LL-E19085γ, LL-E19085ζ and LL-E19085η, to their production by fermentation, to methods for their recovery and concentration from crude solutions and to processes for their purification. The present invention includes within its scope the antibacterial agents in dilute form, as crude concentrates and in pure form. The effect of these new agents on specific microorganisms, together with their chemical and physical properties, differentiate them from previously described antibacterial agents. The structure of antibiotic LL-E19085 is as follows:

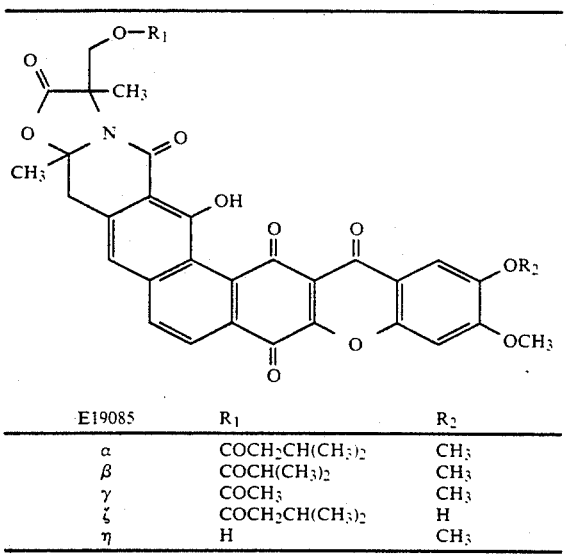

| E19085 | $R_1$ | $R_2$ |
|---|---|---|
| α | $COCH_2CH(CH_3)_2$ | $CH_3$ |
| β | $COCH(CH_3)_2$ | $CH_3$ |
| γ | $COCH_3$ | $CH_3$ |
| ζ | $COCH_2CH(CH_3)_2$ | H |
| η | H | $CH_3$ |

The physiochemical characteristics of antibiotic LL-E19085α are as follows:

a) Molecular formula: $C_{36}H_{31}NO_{12}$;

b) Molecular weight: 669 FABMS $(M+3H)^+ = M/Z$ 672.21176;

c) Elemental Analysis: C, 64.55; H, 4.46; N, 1.92;

d) Specific rotation: $[\alpha]_D^{26} = -52°$ (C, 1.11% - dichloromethane);

e) Ultraviolet absorption spectra:

λmax nm ε0.1N HCl=224 nm (27,700), 255nm (21,900), 328nm (16,400), 420 nm (4,230)

λmax nm ε0.1N NaOH=217 nm (76,100), 340 nm (15,100), 399 nm (12,900)

λmax nm εCH₃OH=222 nm (38,200), 240 nm (30,100), 255 nm (30,100), 321 nm (24,500), 384 nm (8,050)

f) Infrared absorption spectrum: (KBr disk), max (cm⁻¹) 1800, 1742, 1690, 1621, 1422, 1273;

g) Proton magnetic resonance spectrum: (CDCl₃) shows significant peaks as follows:

| δ | #H | M | J(Hz) |
|---|---|---|---|
| 13.47 | 1 | s | — |
| 8.20 | 1 | d | 8.5 |
| 7.92 | 1 | d | 8.5 |
| 7.58 | 1 | s | — |
| 7.19 | 1 | s | — |
| 7.09 | 1 | s | — |
| 4.78 | 1 | d | 11.6 |
| 4.45 | 1 | d | 11.6 |
| 4.02 | 3 | s | — |
| 3.99 | 3 | s | — |
| 3.48 | 1 | d | 12.8 |
| 3.35 | 1 | d | 12.8 |
| 2.21 | 2 | d | 6.8 |
| 2.10 | 1 | m | — |
| 1.83 | 3 | s | — |
| 1.80 | 3 | s | — |
| 0.955 | 6 | d | 6.48 | h) Carbon-13 nuclear magnetic resonance spectrum; (CDCl₃) shows significant peaks as follows:

| δ | M | δ | M | δ | M |
|---|---|---|---|---|---|
| 181.2 | s | 134.8 | s | 65.0 | t |
| 178.1 | s | 132.1 | d | 62.3 | s |
| 172.1* | s | 129.7 | s | 56.8 | q |
| 171.5 | s | 124.4 | d | 56.5 | q |
| 165.8 | s | 120.8 | s | 42.9 | t |
| 162.1 | s | 119.9 | s | 41.9 | t |
| 155.5 | s | 119.5 | s | 25.8 | q |
| 153.4 | s | 117.7 | d | 25.5 | d |
| 150.8 | s | 107.3 | s | 22.4 | q |
| 148.7 | s | 104.9 | d | 22.3 | q |
| 140.7 | s | 100.4 | d | 20.2 | q |
| 137.7 | s | 93.4 | s | | |

*Two superimposed resonances.

The physiochemical characteristics of antibiotic LL-E190857 are as follows:

a) Molecular formula: $C_{35}H_{29}NO_{12}$;

b) Molecular weight: 655;

c) Ultraviolet absorption spectra: λmax (CH₃CN/0.05M pH 4.5 NH₄OAC 3/2) 258 nm, 325 nm, 385 nm;

d) Infrared absorption spectra: λmax (KBr) cm⁻¹ 3434br, 2924, 1804, 1752, 1693, 1621, 1426, 1272;

e) Proton nuclear magnetic resonance spectrum: CDCl₃ shows significant peaks as follows:

| δ | #H | M | J(Hz) |
|---|---|---|---|
| 13.50 | 1 | br | — |
| 8.26 | 1 | d | 8.5 |
| 7.94 | 1 | d | 8.5 |
| 7.66 | 1 | s | — |
| 7.21 | 1 | s | — |
| 7.14 | 1 | s | — |
| 4.77 | 1 | d | 11.6 |
| 4.47 | 1 | d | 11.6 |
| 4.04 | 3 | s | — |
| 4.02 | 3 | s | — |
| 3.50 | 1 | d | 14.8 |
| 3.36 | 1 | d | 14.8 |
| 2.55 | 1 | septet | 7.0 |
| 1.83 | 3 | s | — |
| 1.77 | 3 | s | — |
| 1.19 | 3 | d | 7.0 |
| 1.18 | 3 | d | 7.0 | f) HPLC* retention time: 1.6 minutes.

*Analytical hplc system. The system consisted of a C₁₈ reversed-phase column (2.1 mm × 100 mm) eluted with 60% ACN 40% 0.05M pH 4.5 NH₄OAc at 0.5 ml/min. Detection was by absorbance at 325 nm.

The physiochemical characteristics of antibiotic LL-E19085γ are as follows:

a) Molecular formula: $C_{33}H_{25}NO_{12}$;
b) Molecular weight: 627;
c) Ultraviolet absorption spectra: λmax ($CH_3CN/0.05M$ pH 4.5 $NH_4OAC$ 3/2): 258 nm, 325 nm, 385 nm, 420 nm;
d) Infrared absorption spectrum: λmax (KBr) (cm$^{-1}$: 3433br, 2925, 1805, 1745, 1694, 1621, 1426, 1272;
e) Proton nuclear magnetic resonance spectrum: $CDCl_3$ shows significant peaks as follows:

| δ | #H | M | J(Hz) |
|---|---|---|---|
| 13.46 | 1 | br | — |
| 8.26 | 1 | d | 8.6 |
| 7.94 | 1 | d | 8.6 |
| 7.66 | 1 | s | — |
| 7.21 | 1 | s | — |
| 7.14 | 1 | s | — |
| 4.81 | 1 | d | 11.5 |
| 4.43 | 1 | d | 11.5 |
| 4.04 | 3 | s | — |
| 4.02 | 3 | s | — |
| 3.50 | 1 | d | 14.9 |
| 3.36 | 1 | d | 14.9 |
| 2.10 | 3 | s | — |
| 1.82 | 3 | s | — |
| 1.75 | 3 | s | — | f) HPLC* retention time: 1.6 minutes.
*Analytical hplc system. Same conditions as used in LL-E19085β recited above.

The physiochemical characteristics of antibiotic LL-E19085ζ are as follows:

a) Molecular formula: $C_{35}H_{29}NO_{12}$;
b) Molecular weight: 655;
c) Ultraviolet absorption spectra: λmax ($CH_3CN/0.05M$ pH 4.5 $NH_4OAC$ 3/2): 258 nm, 324 nm, 380 nm, 420 nm;
d) Infrared absorption spectrum: (KBr) λmax (Cm$^{-1}$) 3429(br), 2960, 1805, 1745, 1693, 1626, 1421, 1279;
e) Proton nuclear magnetic resonance spectrum: $CDCl_3$

| δ | #H | M | J(Hz) |
|---|---|---|---|
| 13.45 | 1 | s | — |
| 8.22 | 1 | d | 8.5 |
| 7.91 | 1 | d | 8.5 |
| 7.75 | 1 | s | — |
| 7.26 | 1 | s | — |
| 7.14 | 1 | s | — |
| 6.20 | 1 | br | — |
| 4.76 | 1 | d | 11.5 |
| 4.45 | 1 | d | 11.5 |
| 4.06 | 3 | s | — |
| 3.48 | 1 | d | 14.8 |
| 3.35 | 1 | d | 14.8 |
| 2.20 | 2 | d | 6.6 |
| 2.10 | 1 | septet | 6.6 |
| 1.81 | 3 | s | — |
| 1.75 | 3 | s | — |
| .950 | 6 | d | 6.6 | f) Carbon 13 nuclear magnetic resonance spectra:

| δ | δ |
|---|---|
| 181.4 | 119.7 |
| 178.0 | 119.6 |
| 172.8 | 117.7 |
| 171.7 | 108.4 |
| 171.6 | 107.1 |
| 165.6 | 100.2 |
| 161.6 | 93.4 |
| 154.7 | 64.9 |
| 153.5 | 62.3 |
| 150.2 | 56.5 |
| 146.3 | 42.8 |
| 140.5 | 41.7 |
| 137.5 | 25.6 |
| 134.6 | 25.4 |
| 132.2 | 22.2* |
| 129.7 | 20.0 |
| 124.2 | |
| 120.1 | |

*two superimposed signals g) HPLC* retention time: 1.9 minutes
*Analytical hplc system. Same conditions as in LL-E19085β recited above.

The physiochemical characteristics of antiobiotic LL-E19085η are as follows:

a) Molecular formula: $C_{31}H_{23}NO_{11}$;
b) Molecular weight: 585 HRFABMS:$(M+3H)^+ = M/Z$ 588.1479;
c) Specific rotation: $[\alpha]_D^{260} = -62°$ (C .19)DMSO;
d) Ultra violet absorption spectrum: λmax ($MeOH/CH_2CL_2$ 1:1) 223 (37,800), 321 (21,700), 302 (21,750);
e) Infrared absorption spectrum: (KBr) λmax CM$^{-1}$ 3437(br), 2923, 1798, 1691, 1623, 1427, 1276;
f) Proton nuclear magnetic resonance spectrum; ($CDCl_3$/DMSO $d_6$)

| δ | #H | M | J(Hz) |
|---|---|---|---|
| 8.24 | 1 | d | 8.5 |
| 7.96 | 1 | d | 8.5 |
| 7.63 | 1 | s | — |
| 7.23 | 1 | s | — |
| 7.17 | 1 | s | — |
| 5.28 | 1 | br | — |
| 4.33 | 1 | brd | 10.1 |
| 4.04 | 3 | s | — |
| 4.02 | 3 | s | — |
| 3.90 | 1 | brd | 10.1 |
| 3.51 | 1 | d | 14.7 |
| 3.37 | 1 | d | 14.7 |
| 1.77 | 3 | s | — |
| 1.71 | 3 | s | — | g) Carbon 13 nuclear magnetic resonance spectrum: (DMSO $D_6$/$CDCl_3$)

| δ | δ |
|---|---|
| 180.9 | 107.4 |
| 177.7 | 104.4 |
| 173.0 | 100.7 |
| 171.9 | 93.3 |
| 165.8 | 65.8 |
| 161.4 | 63.4 |
| 155.6 | 56.7 |
| 153.8 | 56.1 |
| 150.8 | 41.4 |
| 148.6 | 25.3 |
| 140.3 | 19.0 |
| 137.3 | |
| 135.2 | |
| 132.2 | |
| 129.6 | |
| 123.9 | |
| 120.2 | |
| 119.3 | |
| 119.2 | |

-continued

| δ | δ |
|---|---|
| 117.6 | | h) HPLC* retention time: 1.2 minutes

*Analytical hplc system. Same conditions as in LL-E19085β recited above.

DETAILED DESCRIPTION OF THE INVENTION

The antibacterial agents LL-E19085α, LL-E19085β, LL-E19085γ, LL-E19085ζ and LL-E19085η are produced by aerobic fermentation of microbial culture LL-E19085 which is a natural selection isolate of a Culture isolated from a soil sample collected in Manyara, Tanzania. The culture was taxonomically characterized and identified as a new subspecies of *Micromonospora citrea*.

This new subspecies is maintained in the culture collection of the Medical Research Division, American Cyanamid Company, Pearl River, N.Y. as culture number LL-E19085. A viable culture of this new microorganism has been deposited with the ARS Culture Collection, Fermentation Laboratory, Northern Regional Research Center, U.S. Department of Agriculture, 1815 North University Street, Peoria, Ill. 61604 and has been added to its permanent collection. It has been assigned the strain designation NRRL 18351 by such depository. Access to such culture, under strain designation NRRL 18351, during pendency of the instant application shall be available to one determined by the Commissioner of Patents and Trademarks to be entitled thereto under 37C.F.R. Section 1.14 and 35U.S.C. Section 122, and all restrictions on availability to the public of such culture will be irrevocably removed upon grant of a patent on the instant application.

Observations were made of the cultural, physiological and morphological features of culture LL-E19085 using methods well known in the art. The generic assignment of LL-E19085 to the genus *Micromonospora* was confirmed morphologically and chemically. The strain produced monospores on the vegetative hyphae. No aerial hyphae were observed. Electron microscopic examination showed that the spores were warty. Whole cell analysis showed that LL-E19085 contained the meso isomer as well as traces of the L isomer of diaminopimelic acid. This strain showed the presence of xylose plus traces of arabinose in its whole cell sugar hydrolysates. Therefore LL-E19085 is considered to be a subspecies of *Micromonospora citrea*.

Comparative data on the morphology of LL-E19085 is given in Tables I and II. Physiological data is given in Tables III and IV.

TABLE I

| ISP Agar Medium | Spores | Vegetative Mycelium | Soluble Pigments |
|---|---|---|---|
| Yeast-Malt (ISP 2) | Slight, black at edge | Strong orange (50) to medium orange-yellow (71*) | Slight, brown-black |
| Oatmeal (ISP 3) | None | Light orange-yellow (70) to vivid orange-yellow (66) | Slight, brownish |
| Inorganic Salts-Starch (ISP 4) | None | Light orange-yellow (70) to vivid orange-yellow (66) | Slight, brownish |
| Glycerol-Asparagine (ISP 5) | Slight, brownish at edge | Light tone of brownish-orange (54) | Slight, brownish |

TABLE I-continued

| ISP Agar Medium | Spores | Vegetative Mycelium | Soluble Pigments |
|---|---|---|---|
| (ISP 5) | edge | (54) | |

*Parenthetical numbers are colors taken from Kelly, K. L. and Judd, D. B., Color, Universal Language and Dictionary of Names, Nat. Bur. Stand. (U.S.), Spec. Publ. 440, 1976, Washington, D.C. and the accompanying Inter-Society Color Council, National Bureau of Standards Centroid Color Charts.

TABLE II

| Agar Medium | Actinomycete Growth (28° C., 2 weeks) |
|---|---|
| Pablum | Brown vegetative hyphae. Sparse spores soluble dark brown pigment. |
| Yeast Czapek's | Brownish tan vegetative hyphae. Sparse spores. Slight soluble dark-brownish pigment. |
| Czapek's | Vegetative hyphae covered/spores. Black spores. Slight dark pigment. |
| Yeast Extract-Dextrose | Black spores. Dry soluble brownish pigment. |
| Nutrient | Orange-brown vegetative hyphae. Sparse black spores. Moderate brown pigment. |
| Nutrient Glycerol | Blackish-tan vegetative hyphae. Sparse spores. Intense brown-black pigment. |
| Bennett's Dextrin | Tan vegetative hyphae. Moderate black spores. Soluble reddish-brown pigment. |
| Glucose Asparagine | Orange-tan vegetative hyphae. No spores. Slight soluble dark pigment. |

TABLE III

| Carbohydrate | Carbohydrate Utilization |
|---|---|
| Arabinose | + |
| Cellulose | − |
| Fructose | ± |
| Glucose | + |
| Inositol | − |
| Mannitol | − |
| Raffinose | − |
| Rhamnose | − |
| Sucrose | ± |
| Xylose | + |

TABLE IV

| Gordon Test | Physiological Reaction |
|---|---|
| Hydrolysis of | |
| Casein | + |
| Xanthine | − |
| Hypoxanthine | − |
| Tyrosine | + |
| Adenine | + |
| Gelatin | + |
| Potato Starch | + |
| Esculin | + |
| Physiological Production of | |
| Nitrate Reductase | − |
| Phosphatase | + |
| Urease | − |
| Growth on | |
| Salicin | − |
| 5% Sodium Chloride | − |
| Lysozyme Broth | − |
| Decarboxylation of | |
| Acetate | + |
| Benzoate | − |
| Citrate | − |
| Lactate | + |
| Malate | − |
| Mucate | − |

TABLE IV-continued

| Gordon Test | Physiological Reaction |
|---|---|
| Oxalate | − |
| Propionate | ± |
| Pyruvate | ± |
| Succinate | − |
| Tartrate | − |
| Acid from | |
| Adonitol | − |
| Arabinose | + |
| Cellobiose | + |
| Dextrin | + |
| Dulcitol | − |
| Erythritol | − |
| Fructose | + |
| Galactose | ± |
| Glucose | + |
| Glycerol | − |
| Inositol | − |
| Lactose | + |
| Maltose | + |
| Mannitol | − |
| Mannose | + |
| α-Methyl-D-glucoside | + |
| Melibiose | + |
| Raffinose | + |
| Rhamnose | − |
| Salicin | − |
| Sorbitol | − |
| Sucrose | + |
| Trehalose | + |
| Xylose | − |
| β-Methyl-D-xyloside | − |
| Growth at | |
| 10° C. | − |
| 42° C. | − |
| 45° C. | − |

+ = positive; − = negative

It is to be understood that for the production of the new antibacterial agents LL-E19085α, LL-E19085β, LL-E19085γ, LL-E19085ζ and LL-E19085η, the present invention is not limited to this particular organism or to organisms fully answering the above growth and microscopic characteristics, which are given for illustrative purposes only. In fact it is desired and intended to include the use of mutants produced from this organism by various means such as exposure to x-radiation, ultraviolet radiation, N'-methyl-N'-nitro-N'-nitrosoguanidine, actinophages and the like.

The in vitro antibacterial effects of antibiotics LL-E19085α, LL-E19085β, LL-E19085γ, LL-E19085ζ and LL-E19085η were determined by standard agar dilution methods against clinical isolates obtained from medical centers representing various geographical areas in the United States. The inoculum of each culture was approximately 1 to 5 × 10⁴ colony forming units applied with a Steers multiple inocula replicator to plates containing the antibiotic in Mueller-Hinton agar. The agar was supplemented with about 5% sheep blood where required for the growth of the organism. The results are given in Tables v and VI.

TABLE V

In vitro Antibacterial Activity of LL-E19085α

| Organism | | Minimal Inhibitory Concentration (mcg/ml) |
|---|---|---|
| Staphylococcus aureus | ATCC 25923 | 0.12 |
| Staphylococcus aureus | Smith | 0.12 |
| Staphylococcus aureus | VGH 84-45 | ≦0.06 |
| Staphylococcus aureus | CMC 83-127 | ≦0.06 |
| Staphylococcus aureus | CMC 83-131 | ≦0.06 |

TABLE V-continued

In vitro Antibacterial Activity of LL-E19085α

| Organism | | Minimal Inhibitory Concentration (mcg/ml) |
|---|---|---|
| Staphylococcus aureus | CMC 83-132 | ≦0.06 |
| Staphylococcus aureus | SSC 82-57 | ≦0.06 |
| Staphylococcus epidermidis | IO 83-58 | ≦0.06 |
| Staphylococcus saphrophiticus | VGH 84-50 | ≦0.06 |
| Streptococcus β-hemolyticus | C 203 | ≦0.06 |
| Streptococcus β-hemolyticus | VGH 84-60 | ≦0.06 |
| Streptococcus β-hemolyticus | VGH 84-61 | ≦0.06 |
| Streptococcus β-hemolyticus | VGH 84-62 | ≦0.06 |
| Streptococcus pneumoniae | SV-1 | ≦0.06 |
| Streptococcus pneumoniae | K 84-21 | ≦0.06 |
| Enterococcus | VGH 84-65 | ≦0.06 |
| Enterococcus | VGH 84-68 | ≦0.06 |
| Enterococcus | IO 83-28 | ≦0.06 |
| Enterococcus | IO 83-40 | 0.12 |
| Enterococcus | CMC 83-72 | ≦0.06 |
| Escherichia coli | No. 311 | >128 |
| Klebsiella pneumoniae | AD | >128 |
| Enterobacter cloacae | VGH 84-37 | >128 |
| Morganella morganii | VGH 84-11 | >128 |
| Serratia marcescens | K 84-14 | >128 |
| Pseudomonas aeruginosa | 12-4-4 | >128 |
| Citrobacter diversis | MOR 84-3 | >128 |
| Proteus vulgaris | CMC 84-35 | >128 |
| Alcaligenes ssp. | ISG 86-34 | >128 |
| erratia rubidea | UHL 86-4 | >128 |
| Bacteroides fragilis | ATCC 25285 | 16 |
| Bacteroides vulgaris | ATCC 29327 | ≦0.06 |
| Bacteroides theta | ATCC 29741 | 4 |
| Bacteroides theta | ATCC 29742 | 4 |
| Clostridium perfringen | ATCC 13124 | ≦0.06 |
| Clostridium differensis | ATCC 17858 | ≦0.06 |
| Peptococcus magnus | ATCC 29328 | ≦0.06 |
| Peptococcus magnus | ATCC 14956 | ≦0.06 |
| Peptococcus asacrolytis | ATCC 29743 | ≦0.06 |
| Escherichia coli | ATCC 25922 | >128 |
| Staphylococcus aureus | ATCC 29213 | ≦0.06 |

TABLE VI

Invitro Antibacterial Activity of LL-E19085...

| Organism | | Minimal Inhibitory Concentration (mcg/ml) | | | |
|---|---|---|---|---|---|
| | | LL-E19085 | LL-E19085 | LL-E19085 | LL-E19085 |
| Staphylococcus aureus | NEMC 87-69 | 4 | 4 | 8 | ≦.015 |
| Staphylococcus aureus | ROSE (MP) | 2 | 1 | 2 | ≦.015 |
| Staphylococcus aureus | IVES 542 | 4 | 8 | 8 | ≦.015 |
| Staphylococcus hemolyticus | AVAH 88-1 | 2 | 8 | 4 | ≦.015 |
| Staphylococcus hemolyticus | AVAH 88-3 | 4 | 0.5 | 2 | ≦.015 |
| Bacteroides cereus | DAVIES | 2 | 0.5 | 2 | ≦.015 |
| Streptococcus faecalis | ARUM 87-41 | 2 | 0.5 | 2 | ≦.015 |
| Enterococcus | CHBM 88-60 | 2 | 0.5 | 2 | ≦.015 |
| Enterococcus | Grp D WRVA 88-33 | 2 | 0.5 | 2 | ≦.015 |
| Streptococcus faecalis | VCI 85-30 | 2 | .06 | 2 | ≦.015 |
| Streptococcus faecalis | VCH 84-69 | 2 | .03 | 2 | ≦.015 |
| Streptococcus faecalis | CMC 83-120 | 2 | 1 | 2 | ≦.015 |
| Streptococcus a-hemolyticus | AMCH 88-84 | 0.5 | ≦.008 | 1 | ≦.015 |
| Streptococcus b-hemolyticus | AMCH 88-86 | 2 | ≦.008 | 2 | ≦.015 |
| Streptococcus pneumoniae | CHBM 88-70 | .25 | ≦.008 | .12 | ≦.015 |
| Streptococcus | CHBB 88-75 | .12 | ≦.008 | .12 | ≦.015 |

TABLE VI-continued

Invitro Antibacterial Activity of LL-E19085...

| Organism | | Minimal Inhibitory Concentration (mcg/ml) | | | |
|---|---|---|---|---|---|
| | | LL-E19085 | LL-E19085 | LL-E19085 | LL-E19085 |
| pneumoniae | | | | | |
| Streptococcus pneumoniae | TEX 85-2 | .12 | ≦.008 | .12 | ≦.015 |
| Staphylococcus aureus | ATCC 29213 | 2 | 1 | 2 | ≦.015 |
| Klebsiella pneumoniae | NEMC 87-271 | ≧64 | ≧16 | ≧32 | ≧32 |
| Escherichia coli | D21 | ≧64 | ≧16 | ≧32 | ≧32 |
| Escherichia coli | D22 | 8 | 16 | 32 | 2 |
| Escherichia coli | ATCC 25922 | >64 | >16 | >32 | >32 |
| Escherichia coli | ATCC 35218 | >64 | >16 | >32 | >32 |
| Staphylococcus aureus | ATCC 25923 | 0.5 | ≧0.008 | 1 | ≦0.015 |
| Staphylococcus aureus | VGH 84-47 | 4 | 1 | 4 | ≦0.015 |
| Staphylococcus aureus | K82-26 | 2 | ≧0.008 | 2 | ≦0.015 |
| Staphylococcus aureus | CMC 83-131 | 4 | 16 | 8 | 0.12 |

When the compounds are employed for the above utility, they may be combined with one or more pharmaceutically acceptable carriers, for example solvents, diluents and the like, and may be administered parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 2 to about 100 mg/kg of animal body weight, preferably given in divided doses two to four times a day, or in sustained release form. For most large mammals the total daily dosage is from about 100 to 750 mg, preferably from about 100 to 500 mg. Dosage forms suitable for internal use comprise from about 100 to 750 mg of the active compound in intimate admixture with liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered by intravenous, intramuscular, or subcutaneous routes. Liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as preserving agents, and antioxidants, for example, vitamin E, ascorbic acid, BHT and BHA.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

General Fermentation Conditions

Cultivation of *Micromonospora citrea sp. LL-E*19085 may be carried out in a wide variety of liquid culture media. Media which are useful for the production of antibiotic LL-E19085α include an assimilable source of carbon, such as starch, sugar, molasses, glycerol, etc.; an assimilable source of nitrogen, such as protein, protein hydrolysate, polypeptides, amino acids, cornsteep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the medium. Aeration is supplied by forcing sterile air through or onto the surface of the fermenting medium. Agitation is provided by a mechanical impeller. An antifoam agent may be added as needed. The growth of the organism is usually conducted at about 24°–37° C., preferably at about 28° C.

The following examples describe the invention in detail.

EXAMPLE 1

Inoculum Preparation

A typical medium used to grow the inocula was prepared according to the following formula:

| Dextrose | 1.0% |
|---|---|
| Dextrin | 2.0% |
| Yeast extract | 0.5% |
| NZ Amine A* | 0.5% |
| Calcium carbonate | 0.1% |
| Defoam agent | 0.3% |
| Water qs | 100% |

*A pancreatic digest of casein, registered trademark of Sheffield Chemical, Norwich, NY.

This medium was sterilized and a 100 ml portion in a 500 ml flask was inoculated with mycelial scrapings from an agar slant of the culture *Micromonospora citrea* sp LL-E19085. The inoculated flask was then placed on a rotary shaker and agitated vigorously for approximately 48 hours at 32° C., providing primary inoculum.

A 100 ml portion of this primary inoculum was then used to inoculate 10 liters of the above sterium medium which was incubated at 32° C. with aeration for 72 hours, providing secondary inoculum.

A 10 liter portion of this secondary inoculum was then used to inoculate 260 liters of the above sterile medium in a tank. This medium was incubated at 32° C. with agitation by an impeller driven at 180 rpm, a sterile air flow of 200 liters per minute and the addition of 50 ml of a defoaming agent for about 48 hours, providing tertiary inoculum.

EXAMPLE 2

Fermentation

A fermentation medium was prepared according to the following formulation:

| | |
|---|---|
| Dextrin | 3.0% |
| Dextrose | 0.5% |
| Nutrisoy | 1.5% |
| Corn steep liquor | 0.5% |
| Calcium carbonate | 0.5% |
| Defoam agent | 0.3% |
| Water qs | 100% |

A 2800 liter portion of the above medium in a tank was sterilized and then inoculated with 300 liters of tertiary inoculum prepared as described in Example 1. Aeration was supplied at the rate of 6.5 liters of sterile air per liter of mash per minute and agitation was supplied by an impeller driven at about 110 rpm. The temperature Was maintained at 28° C. and defoaming agent was added as required. The fermentation was terminated after 129 hours.

EXAMPLE 3

Isolation of Antibiotic LL-E19085α

A 1500 liter portion of the whole harvest mash, prepared as described in Example 2, was mixed with 15 liters of toluene for 30 minutes, then 250 lb of diatomaceous earth was added. After mixing for 15 minutes this mixture was filtered and the cake washed with 150 liters of water. The cake was slurried in a mixture of 208 liters of acetone, 416 liters of dichloromethane and zo liters of 1.5N hydrochloric acid for 2 hours and then filtered. The cake was washed with about 175 liters of dichloromethane with the wash and filtrate combined. The cake was then washed with about 800 liters of water and this wash also combined with the above wash and filtrate and mixed. The dichloromethane layer was separated and washed with an equal volume of water. The dichloromethane layer was separated and concentrated to 100 liters, reextracted with fresh methylene chloride if any aqueous phase was present, and finally concentrated to about 1-3 liters.

The dichloromethane extracts were triturated repeatedly, first with hexane:dichloromethane (9:1) and then with hexane alone to remove the bulk of the fatty impurities giving a brown powder.

Several such partially purified preparations, from fermentations conducted as described in Example 2, totaling 20 g and averaging 10-30α LL-E19085α, were combined and purified by reverse-phase chromatography The column consisted of a 15 liter bed of $C_{18}$ bonded phase packing of 40 micron particle size. The charge was loaded onto the column in 500 ml of acetonitrile:was tetrahydrofuran (1:1). The column was developed at a flow rate of 1.0 liter per minute With a mobile phase consisting of acetonitrile:0.1M pH 4.5 ammonium acetate buffer (8:2). Fractions were collected at approximately 12 minute intervals. Fractions 6 and 7 were combined and evaporated, giving 2.7 g of pure LL-E19085α having the characteristics disclosed in the hereinabove specification.

EXAMPLE 4

Isolation of Antibiotics LL-E190858 and LL-E19085γ

These minor components Were isolated from various side fractions derived from the refining of LL-E19085α from tank fermentations. Chromatography of the material from methylene chloride ($CH_2Cl_2$), extraction of the whole mash on silica gel, and eluting with mixtures of acetone in $CH_2Cl_2$ yielded a fraction enriched in β and γ. This material was dissolved in acetonitrile (ACN) and separated by reversed phase chromatography, NB 7411C99. The column was 21.4 mm×25 cm packed with $C_{18}$ bonded silica. The column was eluted with 60% ACN, 40% 0.05 pH 4.5 Fractions were combined on the basis of analytical hplc to Yield β and γ.

EXAMPLE 5

Isolation of Antibiotic LL-E19085η

An early fraction from the large-scale $C_{18}$ column used to purify E19085α was used to obtain the η component. The material was dissolved in ACN and separated on the 21.4 mm×25 cm $C_{18}$ column eluting with 50% ACN, 50% 0.05M pH 4.5 NH$_4$OAc. Fractions were combined on the basis of analytical hplc to yield E19085η.

EXAMPLE 6

Isolation of LL-E19085ζ

Side fractions from silica gel purification of E19085α were enriched in E19085( (NB7411C73) The fraction containing zeta was recbromatograpbed on silica gel (150 g Wolen, column 2.5×50 cm) eluted with $CH_2Cl_2$ followed by 5% acetone 95% $CH_2Cl_2$. Fractions were combined on the basis of analytical hplc and evaporated to dryness to yield E19085ζ. (7580C151)

We claim:
1. A biologically pure culture of *Micromonospira citrea sp.* NRRL 18351 or mutants thereof which retain the ability to synthesize antibiotic LL-E19085 a.

* * * * *